(12) United States Patent
Cornes

(10) Patent No.: US 6,924,250 B2
(45) Date of Patent: Aug. 2, 2005

(54) HERBICIDAL COMPOSITION

(75) Inventor: Derek Cornes, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/658,697

(22) Filed: Sep. 9, 2003

(65) Prior Publication Data

US 2004/0048746 A1 Mar. 11, 2004

Related U.S. Application Data

(63) Continuation of application No. PCT/GB02/02534, filed on Jun. 6, 2002.

(30) Foreign Application Priority Data

Jun. 11, 2001 (GB) .............................................. 0114198

(51) Int. Cl.$^7$ .................. A01N 35/06; A01N 41/10; A01N 43/90
(52) U.S. Cl. .................. 504/136; 504/241; 504/350
(58) Field of Search ................................ 504/136, 241, 504/350

(56) References Cited

U.S. PATENT DOCUMENTS 6,486,096 B1 * 11/2002 Hacker et al. .............. 504/133

FOREIGN PATENT DOCUMENTS

| FR | 2 781 983 | * | 2/2000 |
|---|---|---|---|
| WO | 91 05469 | | 5/1991 |
| WO | 95 28839 | | 11/1995 |
| WO | 97 03562 | | 2/1997 |
| WO | 97 48276 | | 12/1997 |
| WO | 02 17719 | | 3/2002 |
| WO | 02 21920 | | 3/2002 |

* cited by examiner

Primary Examiner—S. Mark Clardy
(74) Attorney, Agent, or Firm—Rose M. Allen

(57) ABSTRACT

The present invention relates to a synergistic herbicidal composition comprising;
(A) mesotrione, and:
(B) a second herbicide selected from; (B1) triazines (B2) triazolinones (B3) triazinones (B4) imidazolinones (B5) dicamba (B6) flumetsulam (B7) trifloxysulfuron (B8) tritosulfuron (B9) triasulfuron (B10) pyriftalid (B11) prosulfocarb (B12) pretilachlor (B13) cinosulfuron, or their herbicidally effective salts.

A method of controlling the growth of undesirable vegetation, particularly in crops, using this synergistic composition is also disclosed.

8 Claims, No Drawings

HERBICIDAL COMPOSITION

This application is a continuation of pending International Application No. PCT/GB02/02534, filed Jun. 6, 2002, the contents of which are incorporated herein by reference.

The present invention relates to a herbicidal composition containing (A) mesotrione and (B) a second herbicidal compound. The invention also relates to a method of controlling the growth of undesirable vegetation, particularly in crops, using this composition.

The protection of crops from weeds and other vegetation that inhibits crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually, and this is referred to as "synergism." As defined in the *Herbicide Handbook* of the Weed Science Society of America, Seventh Edition, 1994, page 318, "'synergism'[is] an interaction of two or more factors such that the effect when combined is greater than the predicted effect based on the response to each factor applied separately." The present invention is based on the discovery that mesotrione and certain other herbicides display a synergistic effect when applied in combination.

The herbicidal compounds forming the synergistic composition of this invention are independently known in the art for their effects on plant growth. They are all disclosed in The Pesticides Manual, Twelfth Edition, 2000, published by The British Crop Protection Council. They are also commercially available.

The present invention relates to a synergistic herbicidal composition comprising;
(A) mesotrione, and:
(B) a second herbicide selected from;
(B1) triazines
(B2) triazolinones
(B3) triazinones
(B4) imidazolinones
(B5) dicamba
(B6) flumetsulam
(B7) trifloxysulfuron
(B8) tritosulfuron
(B9) triasulfuron
(B10) pyriftalid
(B11) prosulfocarb
(B12) pretilachlor
(B13) cinosulfuron
or their herbicidally effective salts.

The synergistic compositions of the present invention can provide one or more of a number of advantages over the use of the individual components (A) and (B). The rates of application of the individual components can be markedly reduced while maintaining a high level of herbicidal efficacy. The composition can have a considerably broader weed spectrum against which it is effective than does either of the components alone. The composition can have the potential to control weed species at a low application rate at which the individual compounds alone were ineffective. The composition can have a speed of action which is faster than that which would have been predicted from the speed of the individual components.

The composition contains a herbicidally effective amount of a combination of component (A) and component (B). The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits.

Mesotrione can be used in the form of a salt or metal chelate, such as a copper chelate. Most preferably, the mesotrione is in the form of a copper chelate. Metal chelates of mesotrione and their preparation are known and described in U.S. Pat. No. 5,912,207.

Triazines are compounds of the general formula;

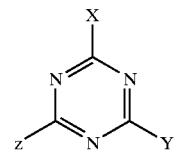

in which X is selected from halo, C1–6 alkoxy, or C1–6 alkylmercapto, Y and Z are independently selected from C1–6 alkylamino, C1–6 dialkylamino. Preferably X is chloro, methylmercapto or methoxy. Preferably Y and Z are independently ethylamino, isopropylamino, or tertiarybutylamino. Examples of triazines are ametryne, atrazine cyanazine, desmetryne, dimethametryne, prometron, prometryne, propazine, terbumeton, terbutryne trietazine, terbuthylazine, simazine and simetryne. Most preferably the triazine is terbuthylazine or simazine.

Triazolinones are compounds such as amicarbazone.

Triazinones are compounds such as hexazinone or compounds of formula;

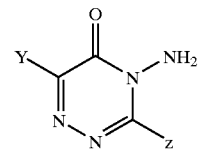

in which Y is an alkyl, for example C1–8 alkyl, preferably C2–6 alkyl, or Y is cycloalkyl, for example C5–7 cycloalkyl, preferably cyclohexyl, or Y is aryl, for example phenyl, and Z is alkyl, for example C1–6 alkyl, preferably methyl, or Z is alkoxy or alkyl thio, for example C1–6 alkoxy or C1–6 alkylmercapto, preferably methylmercapto. Examples of triazolinones are metamitron, and metribuzin.

Imidazolinones are compounds of formula;

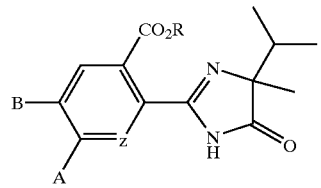

in which Z is CH or N, B is H, C1–6 alkyl, or C1–6 alkoxy C1–6 alkyl, B is H, or A and B together form an aromatic ring.

Preferably Z is N. Preferably B is methyl, ethyl or methoxyethyl, or A and B are an unsubstituted aromatic ring.

Examples of imidazolinones are imazapic, imazapyr, imazamethabenz-methyl, imazaquin, imazamox and imazethapyr Dicamba can be in the form of a salt such as a sodium, potassium or ammonium salt.

Trifloxysulfuron can be in the form of a salt, such as a sodium salt.

Preferably, component (B) is terbuthylazine, simazine, dicamba, flumetsulam, imazamox, imazapyr, imazethapyr, metribuzin, trifloxysulfuron or pyriftalid, with terbuthylazine and simazine being especially preferred. Additional herbicides can also be added to the mixtures. For example, sulphonyl ureas such as nicosulfuron, prosulfuron, bensulfuron can be added to the mixture of mesotrione and pyriftalid for use in rice.

The invention also relates to a method of controlling the growth of undesirable vegetation, particularly in crops, and to the use of this synergistic composition.

The species spectrums of the compounds (A) and (B), i.e., the weed species that the respective compounds control, are broad and highly complementary. Mesotrione controls most broadleaf weeds and a few grass weeds, and compounds (B) control most grass weeds and a few or some broadleaf weeds. The species spectrum for individual compounds within the scope of each formula varies to some extent. It has been surprisingly found, however, that a combination of a compounds (A) and (B) exhibits a synergistic action in the control of many common weeds.

In the compositions of this invention, the weight ratio of component (A) to component (B) at which the herbicidal effect is synergistic lies within the range of between about 32:1 and about 1:20. Preferably, the weight ratio of component (A) to component (B) is between about 8:1 and 1:15, with a weight ratio of between about 4:1 and about 1:10 being especially preferred.

The rate at which the synergistic composition of the invention is applied will depend upon the particular type of weed to be controlled, the degree of control required, and the timing and method of application In general the composition of the invention can be applied at an application rate of between about 0.005 kilograms/hectare (kg/ha) and about 5.0 kg/ha, based on the total amount of active ingredient (component (A)+component (B)) in the composition. An application rate of between about 0.5 kg/ha and 3.0 kg/ha is preferred. In an especially preferred embodiment of this invention, the composition contains components (A) and (B) in relative amounts sufficient to provide an application rate of at least 1.0 kg/ha, of which component (A) provides at least 0.02 kg/ha.

The compositions of this invention are useful as herbicides, demonstrating synergistic activity for the control of undesirable vegetation. The compositions can be formulated in the same manner in which herbicides are generally formulated. The compounds may be applied either separately or combined as part of a two-part herbicidal system.

The object of the formulation is to apply the compositions to the locus where control is desired by a convenient method. The "locus" is intended to include soil, seeds, and seedlings, as well as established vegetation.

The composition can be used over a wide range of crops, such as corn (maize), wheat, rice, potato or sugarbeet. Suitable crops include those which are tolerant to one or more of components (A) or (B), or to any other herbicide, such as glyphosate that can be additionally included in the composition. The tolerance can be natural tolerance produced by selective breeding or can be artificially introduced by genetic modification or the crop. Tolerance means a reduced susceptibility to damage caused by a particular herbicide compared to the conventional crop breeds. Crops can be modified or bred so as to be tolerant, for example to HPPD inhibitors like mesotrione, or EPSPS inhibitors like glyphosate. Corn (maize) is inherently tolerant to mesotrione The composition employed in the practice of the present invention can be applied in a variety of ways known to those skilled in the art, at various concentrations. The composition is useful in controlling the growth of undesirable vegetation by preemergence or postemergence application to the locus where control is desired. The compositions of the present invention are particularly effective when applied preemergence.

The synergistic herbicidal compositions of this invention preferably also comprise an agriculturally acceptable carrier therefor. In practice, the composition is the industry for facilitating dispersion. The choice of formulation and mode of application for any given compound may affect its activity, and selection will be made accordingly. The compositions of the invention may thus be formulated as granules, as wettable powders, as emulsifiable concentrates, as powders or dusts, as flowables, as solutions, as suspensions or emulsions, or as controlled release forms such as microcapsules. These formulations may contain as little as about 0.5% to as much as is about 95% or more by weight of active ingredient. The optimum amount for any given compound will depend upon formulation, application equipment, and nature of the plants to be controlled.

Wettable powders are in the form of finely divided particles that disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, filler's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids that act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents, when used, normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as disking, dragging or mixing operations.

If necessary or desired for a particular application or crop, the composition of the present invention may contain an antidotally effective amount of an antidote for component (A) or component (B). Those skilled in the art will be familiar with suitable antidotes. Examples of suitable antidotes are benoxacor and cloquintocet mexyl.

Further, other biocidally active ingredients or compositions may be combined with the synergistic herbicidal composition of this invention. For example, the compositions may contain, in addition to components (A) and (B), insecticides, fungicides, bactericides, acaracides or nematicides, in order to broaden the spectrum of activity.

As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of individual and combined herbicides, the application rate of any antidote, and the ratio of the individual herbicides to one another and/or to an antidote, as well as the nature of crops or weeds being tested, can affect the results of the test. Results may vary from crop to crop within the crop varieties.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined by the appended claims.

What is claimed is:

1. A synergistic herbicidal composition comprising (A) mesotrione, and (B), flumetsulam, or its herbicidally effective salts.

2. An herbicidal composition according to claim 1, wherein the weight ratio of component (A) to component (B) is between about 32:1 and about 1:20.

3. An herbicidal composition according to claim 2, wherein the weight ratio of component (A) to component (B) is between about 8:1 and 1:15.

4. An herbicidal composition according to claim 3, wherein the weight ratio of component (A) to component (B) is between about 4:1 and about 1:10.

5. A method for controlling undesirable vegetation, comprising applying to the locus of such vegetation a herbicidally effective amount of a composition as claim 1.

6. A method according to claim 5, wherein the combined amount of components (A) and (B) applied to the locus of the undesirable vegetation is between about 0.005 kg/ha and about 5.0 kg/ha.

7. A method according to claim 6, wherein the combined amount of components (A) and (B) applied to the locus of the undesirable vegetation is between about 0.5 kg/ha and 3.0 kg/ha.

8. A method according to claim 5, wherein the combined amount of components (A) and (B) applied to the locus of the undesirable vegetation is at least 1.0 kg/ha, and wherein at least 0.02 kg/ha of component (A) is applied to the locus of the undesirable vegetation.

* * * * *